US007105483B2

(12) United States Patent
Cotton et al.

(10) Patent No.: US 7,105,483 B2
(45) Date of Patent: Sep. 12, 2006

(54) PHOSPHINIC PSEUDOPEPTIDE DERIVATIVES FOR THE SELECTIVE INHIBITION OF THE C-TERMINAL ACTIVE SITE OF ANGIOTENSIN I CONVERTING ENZYME (ACE)

(75) Inventors: Joel Cotton, Orsay (FR); Dimitri Georgiadis, Athens (GR); Vincent Dive, Palaiseau (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 10/500,891

(22) PCT Filed: Jan. 16, 2003

(86) PCT No.: PCT/FR03/00129

§ 371 (c)(1),
(2), (4) Date: Jul. 7, 2004

(87) PCT Pub. No.: WO03/062247

PCT Pub. Date: Jul. 31, 2003

(65) Prior Publication Data

US 2005/0070505 A1 Mar. 31, 2005

(30) Foreign Application Priority Data

Jan. 18, 2002 (FR) .................................. 02 00599

(51) Int. Cl.
*A61K 38/00* (2006.01)
*A61K 38/02* (2006.01)
*A61K 38/05* (2006.01)

(52) U.S. Cl. ................................ 514/7; 514/2; 514/19

(58) Field of Classification Search ..................... None
See application file for complete search history.

(56) References Cited

U.S. PATENT DOCUMENTS

| | | | | |
|---|---|---|---|---|
| 5,476,847 | A * | 12/1995 | McKittrick et al. | 514/80 |
| 5,500,414 | A * | 3/1996 | Dive et al. | 514/18 |
| 5,776,903 | A * | 7/1998 | Dive et al. | 514/18 |
| 6,482,797 | B1 * | 11/2002 | Dive et al. | 514/2 |

FOREIGN PATENT DOCUMENTS

| | | | |
|---|---|---|---|
| EP | 0 361 341 | | 4/1990 |
| EP | 361341 | A2 * | 4/1990 |
| EP | 0 725 075 | | 8/1996 |
| FR | 2 676 059 | | 11/1992 |
| FR | 2 781 230 | | 1/2000 |
| WO | WO 200001706 | A1 * | 1/2000 |

OTHER PUBLICATIONS

Demange, L. et al. "Synthesis of phosphinic alanyl-proline surrogates Ala psi (P02R-CH) Pro as potential inhibitors of the human cyclophilin hCyp-18", Tetrahedron Letters, Elsevier Science Publishers, Amsterdam, NL, vol. 42, no. 36, pp. 6295-6297, XP004302932, ISSN: 0040-4039, Sep. 3, 2001.

Dzau, Victor J. "Tissue Angiotensin and Pathobiology of Vascular Disease: A Unifying Hypothesis", Hypertension. vol. 37, pp. 1047-1052 2001.

Linz, Wolfgang et al. "Contribution of Kinins to the Cardiovascular Actions of Angiotensin-Converting Enzyme Inhibitors" Pharmacological Reviews. vol. 47, no. 1, pp. 25-49 1995.

Soubrier, Florent et al, "Two putative active centers in human angiotensin I-converting enzyme revealed by molecular cloning", Biochemistry, vol. 85 pp. 9386-9390 1998.

Wei, Lei et al. "The Two Homologous Domains of Human Angiotensin I-converting Enzyme are Both Catalytically Active", The Journal of Biological Chemistry, vol. 266, No. 14, pp. 9002-9008, 1991.

Jaspard, Emmanuel et al. "Differences in the Properties and Enzymatic Specificities of the Two Active Sites of Angiotensin I-converting Enzyme (Kininase II)", The Journal of Biological Chemistry, vol. 268, No. 13, pp. 9496-9503 1993.

Azizi, Michel et al. "Acute Angiotensin-converting Enzyme Inhibition Increases the Plasma Level of the Natural Stem Cell Regulator N-Acetyl-Seryl-Aspartyl-Lysyl-Proline", J. Clin. Invest., vol. 97, No. 3, pp. 839-844 1996.

Dive, Vincent et al. "RXP 407, a phosphinic peptide, is a potent inhibitor of angiotensin I converting enzyme able to differentiate between its two active sites", Biochemistry, vol. 96, pp. 4330-4335 1999.

Junot, Christophe et al. "RXP 407, a Selective inhibitor of the N-Domain of Angiotensin I-Converting Enzyme, Blocks in Vivo the Degradation of Hemoregulatory Peptide Acetyl-Ser-Asp-Lys-Pro with No Effect on Angiotensin I Hydrolysis", The Journal of Pharmacology and Experimental Therapeutics, vol. 297, No. 2, pp. 606-611 2001.

Jiracek, Jiri et al. "Development of Highly Potent and Selective Phosphinic Peptide Inhibitors of Zinc Endopeptidase 24-15 Using Combinatorial Chemistry", The Journal of Biological Chemistry, vol. 270, No. 37, pp. 21701-21706 1995.

(Continued)

*Primary Examiner*—Bruce R. Campell
*Assistant Examiner*—Andrew D. Kosar
(74) *Attorney, Agent, or Firm*—Oblon, Spivak, McClelland, Maier & Neustadt, P.C.

(57) ABSTRACT

The invention relates to the use of phosphinic pseudopeptide derivatives for production of a medicament for selectively inhibiting the active C-terminal site of angiotensin I converting enzyme. These derivatives are of formula (II):

(II)

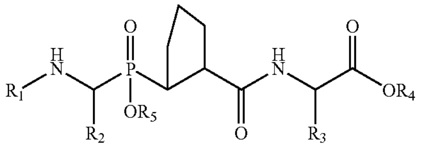

where, $R_1$ may be a protecting group for amino functions usually used in peptide chemistry or an amino acid or a peptide protected by the above type of protecting groups, $R_2$ and $R_3$ correspond to a natural or unnatural amino acid side chain and $R_4$ and $R_5$ represent a hydrogen atom or a counterion.

25 Claims, 3 Drawing Sheets

OTHER PUBLICATIONS

Jiracek, Jiri et al. "Development of the First Potent and Selective Inhibitor of the Zinc Endopeptidase Neurolysin Using a Systematic Approach Based on Combinatorial Chemistry of Phosphinic Peptides", The Journal of Biological Chemistry, vol. 271, No. 32, pp. 19606-19611 1996.
Yiotakis, Athanasios et al. "Protection of the Hydroxyphosphinyl Function of Phosphinic Dipeptides by Adamantyl. Application to the Solid-Phase Synthesis of Phosphinic Peptides", The Journal of Organic Chemistry, vol. 61, No. 19, pp. 6601-6605 1996.
Vassiliou, Stamatia et al. "Phosphinic Pseudo-Tripeptides as Potent Inhibitors of Matrix Metalloproteinases: A Structure-Activity Study", Journal of Medicinal Chemistry, vol. 42, No. 14, pp. 2610-2620 1999.
Georgiadis, Dimitris et al. "Potent and Selective Inhibition of Zinc Aminopeptidase A (EC 3.4.11.7, APA) by Glutamyl Aminophosphinic Peptides: Importance of Glutamyl Aminophosphinic Residue in the P1 Position", Biochemistry, vol. 39, No. 5, pp. 1152-1155 2000.
Greene, Theodora W. et al. "The Role of Protective Groups in Organic Synthesis" and "Protection for the Amino Group", Protective Groups in Organic Synthesis, $2^{nd}$ ed., pp. 1, 309-315 1991.
Baylis, E. et al. "1-Aminoalkylphosphonous Acids. Part 1. Isosteres of the Protein Amino Acids", J. Chem.Soc. Perkin Trans., pp. 2845-2853 1984.
Villieras, J. et al. "The Wittig-Homer Reaction in Heterogenous Media VIII. Cyclisation During the Aldolisation Step from Aqueous Glutaraldehyde", pp. 149-157 1986.
Chen, Huixiong et al. "Long Lasting Antinociceptive Properties of Enkephalin Degrading Enzyme (NEP and APN) Inhibitor Prodrugs", J. Med. Chem., vol. 44, pp. 3523-3530 2001.

* cited by examiner 1a-c 2 3a-c 3a-c 4a-c 4a-c 5a-c 5a-c 6a-c

FIG. 3
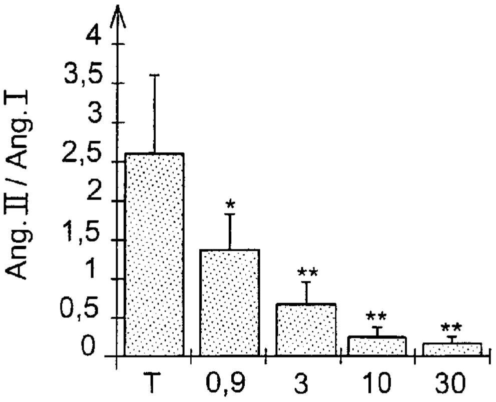
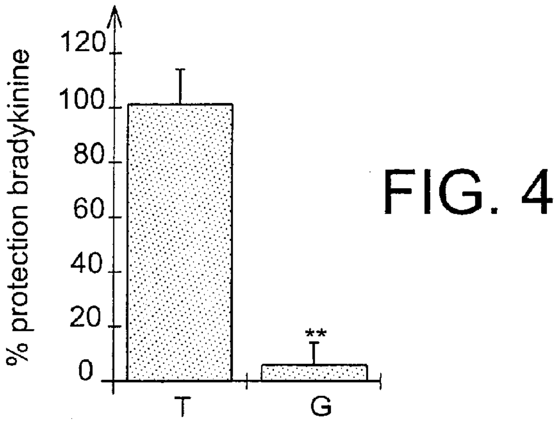
FIG. 4
FIG. 5
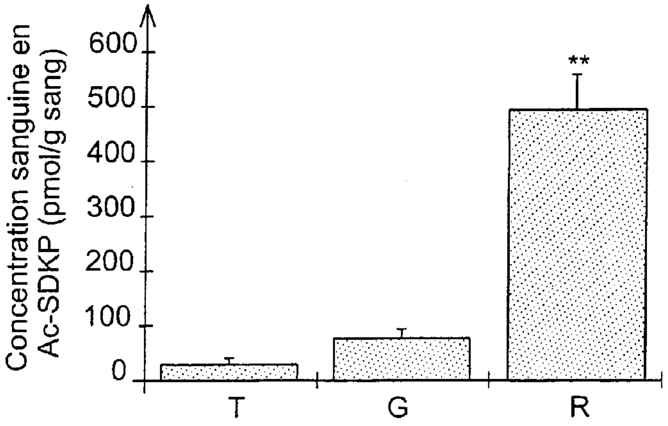

PHOSPHINIC PSEUDOPEPTIDE DERIVATIVES FOR THE SELECTIVE INHIBITION OF THE C-TERMINAL ACTIVE SITE OF ANGIOTENSIN I CONVERTING ENZYME (ACE)

TECHNICAL FIELD

The present invention relates to the use of phosphinic pseudopeptide derivatives for the preparation of a medicinal product for selectively inhibiting the C-terminal active site of human angiotensin I converting enzyme (ACE), i.e. without affecting the N-terminal active site of ACE.

Such a medicinal product may be used in the prevention and treatment of various cardiovascular pathologies in man.

The present invention also relates to novel phosphinic pseudopeptide derivatives, to pharmaceutical compositions containing them and to processes for preparing the said phosphinic pseudopeptide derivatives.

PRIOR ART

Angiotensin I converting enzyme (ACE) is a central component in the regulation of arterial pressure and in the homeostasis of the various physiological functions of cardiovascular tissue. These actions appear to depend partly on:

- the maturation of a powerful vasoconstrictor, angiotensin II, via cleavage of the C-terminal end of angiotensin I, the inactive peptide, with ACE, and
- the degradation via ACE of a powerful vasodilator, bradykinin.

These actions are illustrated below.

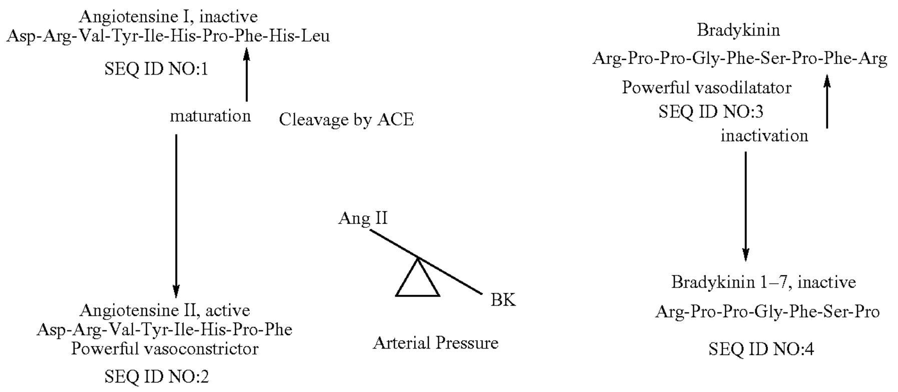

Arterial hypertension, and also cardiac tissue diseases, result from deregulation of the various vasoconstrictive hormones. Re-establishing the equilibrium between vasoconstrictors and vasodilators, for the benefit of the latter, is one of the main therapeutic objectives of the medicinal products used in human clinical treatment to remedy arterial hypertension and cardiac tissue diseases. It is thus understood how the inhibition of ACE can participate towards these objectives, by preventing the formation of angiotensin II and potentiating bradykinin. ACE inhibitors are used in human clinical treatment not only to reduce arterial hypertension, but also to preserve the functions of cardiac tissue, as described in references [1] and [2].

The cloning of ACE followed by the determination of its primary structure showed, surprisingly, the presence of two active sites in this enzyme, as described in reference [3]. Via site-directed mutagenesis, it has been possible to prove that these two active sites are fully functional, i.e. capable of cleaving physiological substrates of ACE, such as angiotensin I and bradykinin (references [4] and [5]).

Despite all the studies performed for more than 20 years on ACE, it is still not known whether the presence of two active sites in mammalian ACE, resulting from duplication of an ancestral gene, corresponds to a particular functional role. However, the recent discovery that, in vivo, in man, the peptide Ac-SDKP (N-acetyl Ser-Asp-Lys-Pro) (SEQ ID NO:5) is essentially cleaved via the N-terminal active site of ACE, argues in favor of a distinct functional role for each of the active sites of ACE (reference [6]).

These considerations have led researchers to attempt to develop inhibitors capable of highly selectively discriminating between the two active sites of ACE, in order to furnish tools capable of establishing in vivo the functional role of each of the sites of ACE.

In this regard, it is important to underline that all the inhibitors used to date in clinical studies are mixed ACE inhibitors, i.e. inhibitors that simultaneously block the two active sites of ACE.

The first inhibitor that selectively blocks the N-terminal site of ACE, RXP407, which is a phosphinic pseudopeptide, has recently been developed (references [7] and [8]). This inhibitor, which is not metabolized in rats and mice, is, moreover, capable of inhibiting the degradation of the peptide N-acetyl Ser-Asp-Lys-Pro (Ac-SDKP) (SEQ ID NO:5) in vivo in mice (reference [9]). Thus, the injection of RXP407, by blocking the N-terminal site of ACE, would prevent the in vivo degradation of Ac-SDKP.

This inhibitor forms the subject of a preclinical study in the said animal, which is directed towards demonstrating its usefulness for protecting haematopoietic tissue during chemotherapy treatment.

However, no inhibitor capable of discriminating between the two active sites of ACE by interacting essentially with the C-terminal site of ACE has been described to date. However, it would be desirable to have available such inhibitors. The reason for this is that, besides their value in experimental and clinical research, they would have the major advantage, over standard mixed ACE inhibitors, of not interfering with the physiological functions associated with the activity of the N-terminal site of ACE, for instance the metabolism of the peptide Ac-SDKP.

It has been demonstrated that phosphinic peptides represent a generic family of compounds capable of very strongly inhibiting zinc metallopeptidases, the peptidase family to which ACE belongs, as may be seen in references [9] to [16]. In these compounds, the role of the $PO_2^-$ group is to interact with the zinc atom located in the active site of these enzymes.

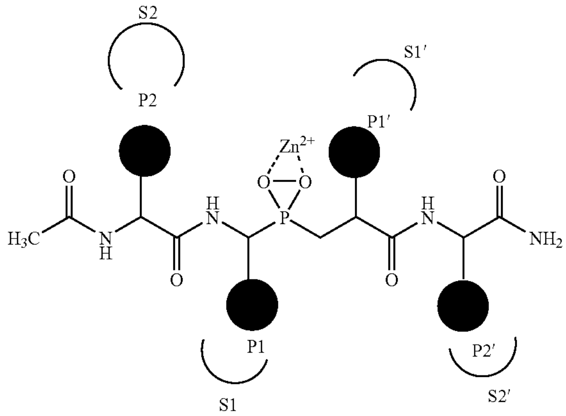

Besides the presence of the $PO_2^-$ group, the chemical nature of the residues P2, P1, P1' and P2' plays a deciding role in ensuring the selectivity of the interactions between a particular phosphinic peptide and a given zinc metallopeptidase (see references [8], [12] and [13]). Thus, the presence of quite specific residues in positions P2, P1, P1' and P2' makes it possible to obtain selective inhibitors, which inhibit only certain zinc metallopeptidases. Such selectivity may be an essential factor in the context of an in vivo use of these inhibitors. Specifically, it is estimated that the in vivo toxicity of certain inhibitors is predominantly due to their lack of selectivity for a given target.

According to these principles, the search for inhibitors capable of selectively blocking the C-terminal site of ACE consisted in identifying, in the family of phosphinic compounds, particular residues located in positions P1, P1' and P2', which give the inhibitors the capacity to selectively interact with the C-terminal site of ACE.

DESCRIPTION OF THE INVENTION

This research has led to the discovery that the presence of a pseudoproline residue in phosphinic pseudopeptides constitutes an essential element for obtaining selective inhibitors of the C-terminal site of ACE.

Thus, one subject of the present invention is the use of at least one phosphinic pseudopeptide derivative comprising the amino acid sequence of formula (I) below:

(I)

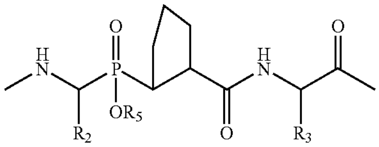

in which:

$R_2$ and $R_3$, which are identical or different, represent the side chain of a natural or unnatural amino acid, the sequence:

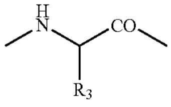

also possibly forming the Pro (proline) residue, and $R_5$ represents a hydrogen atom, a pharmacologically acceptable counterion, or a group capable of forming an in vivo hydrolysable phosphinic ester;

for the manufacture of a medicinal product capable of selectively inhibiting the C-terminal site of angiotensin I converting enzyme.

In this sequence, the $PO_2$ group may be in the form $PO_2^-$ by being associated with a hydrogen atom or a pharmacologically acceptable counterion, for example $K^+$, $Na^+$, $NH_4^+$ or any other pharmacologically acceptable metal or non-metal ion. The nature of the counterion is irrelevant since, in water, the charged groups are dissociated.

The $PO_2$ group may also be in the form of phosphinic ester hydrolysable in vivo. In this case, the pseudopeptide is of the prodrug type, and, after in vivo hydrolysis of the ester, it generates the active form of the pseudopeptide.

Groups of this type that may be used for $R_5$ are described in particular in reference [20].

Examples of such groups that may be mentioned are groups corresponding to the following formulae:

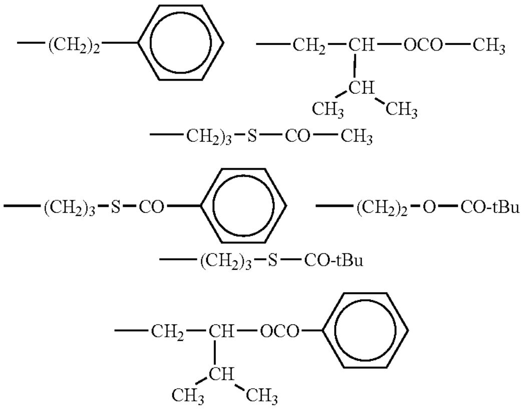

In these formulae, t-Bu represents the tert-butyl group.

According to one particular embodiment of the invention, the phosphinic pseudopeptide derivative corresponds to formula (II) below:

(II)

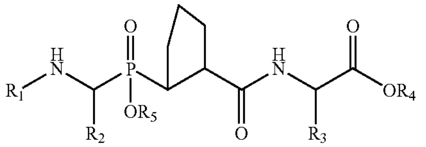

in which:

- $R_1$ represents a protecting group for an amine function, or an amino acid or a peptide protected with a protecting group for an amine function,
- $R_2$ and $R_3$, which may be identical or different, represent the side chain of a natural or unnatural amino acid, the sequence:

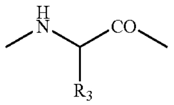

also possibly forming the Pro residue,

- $R_4$ represents a hydrogen atom or a pharmacologically acceptable counterion, and
- $R_5$ is as defined above.

In the formulae given above, $R_2$ and $R_3$ represent the side chain of a natural or unnatural amino acid, for example a pseudoamino acid.

The natural amino acids may be chosen from alanine, arginine, asparagine, aspartic acid, cysteine, glutamine, glutamic acid, glycine, histidine, isoleucine, leucine, norleucine, lysine, methionine, phenylalanine, proline, hydroxyproline, serine, threonine, tryptophan, tyrosine, valine, nitrophenylalanine, homoarginine, thiazolidine and dehydroproline.

A pseudoamino acid may be defined as an amino acid in which the amino or carbonyl function has been replaced with another chemical group.

In formula (II) mentioned above, the group $R_1$ may be a common protecting group for an amine function in peptide chemistry. Such protecting groups are well known to those skilled in the art and are illustrated, for example, in the book entitled "Protective Groups in Organic Synthesis", Second Edition, T. W. Greene and P. G. M. Wuts, John Wiley & Sons, Inc., pages 309–315 [17]. As examples of such groups that may be used in the invention, mention may be made of acetyl and benzyloxycarbonyl groups.

$R_1$ may also represent a natural or unnatural amino acid or a peptide whose terminal amine function is protected with a common protecting group such as those described above.

According to the invention, as will be seen herein-below, the presence of the pseudoproline residue is essential to obtain the selectivity towards the C-terminal active site of ACE, but the nature of the side chains present in $R_2$ and $R_3$ also plays an important role in the selectivity of the interactions of the derivatives used according to the invention with the N-terminal and C-terminal sites of ACE.

Good results as regards the inhibition of the C-terminal site of ACE have been obtained with pseudopeptides in which the group $R_2$ represents the benzyl, methyl or phenylethyl group, i.e. the side chain of phenylalanine, alanine and homophenylalanine.

For $R_3$, good results have been obtained when $R_3$ represents the side chain of alanine, arginine or tryptophan, or when the sequence —NH—CH($R_3$)—CO— represents a Pro residue.

Generally, $R_4$ and $R_5$ represent a hydrogen atom.

According to one preferred embodiment of the invention, the phosphinic pseudopeptide derivative corresponds to the following formula:

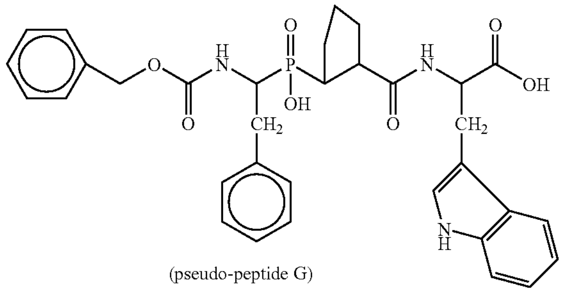

(pseudo-peptide G)

The phosphinic pseudopeptide derivatives that may be used in accordance with the invention have been found to be capable of selectively inhibiting the C-terminal active site of angiotensin I converting enzyme, and thus of controlling in vivo the physiological levels of angiotensin II—which plays a central role in controlling arterial pressure and homeostasis of the cardiovascular functions in man—without, however, interfering with the metabolism of bradykinin or with that of the peptide Ac-SDKP.

Their use as active principles in a medicinal product is thus liable to find numerous applications in the prevention and treatment of human cardiovascular pathologies, and especially pathologies in which bradykinin is thought to take little part, for instance the prevention of atherosclerosis.

Among the phosphinic pseudopeptide derivatives whose use is envisaged according to the invention, some of them have never been described in the literature.

Thus, a subject of the invention is also a phosphinic pseudopeptide derivative comprising the amino acid sequence of formula (I) mentioned above, in which:

- $R_2$ represents the side chain of a natural or unnatural amino acid,
- the sequence:

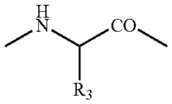

forms the Pro residue:

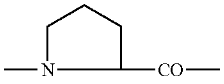

and

- $R_5$ represents a hydrogen atom, a pharmacologically acceptable counterion or a group capable of forming an in vivo hydrolysable phosphinic ester.

Among these derivatives, the ones that are especially preferred are those corresponding to the formula (II) mentioned above, in which:

- $R_1$ represents a protecting group for an amine function, or an amino acid or a peptide protected with a protecting group for an amine function,
- $R_2$ represents the side chain of a natural or unnatural amino acid,
- the sequence:

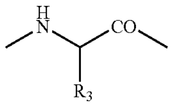

forms the Pro residue:

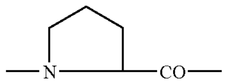

$R_4$ represents a hydrogen atom or a pharmacologically acceptable counterion, $R_5$ represents a hydrogen atom, a pharmacologically acceptable counterion or a group capable of forming an in vivo hydrolysable phosphinic ester.

More particularly, the preferred phosphinic pseudopeptide derivative is the one of formula:

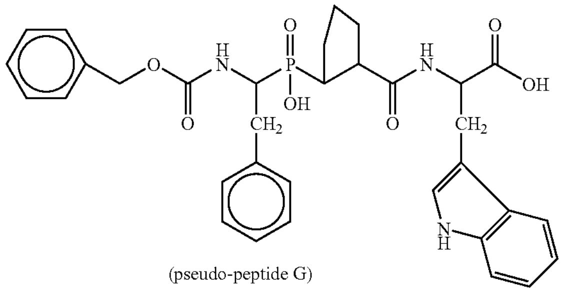

(pseudo-peptide G)

A subject of the invention is also a pharmaceutical composition comprising at least one phosphinic pseudopeptide derivative corresponding to formula (II) mentioned above, in which:

$R_2$ represents the side chain of a natural or unnatural amino acid, the sequence:

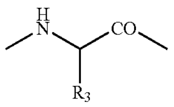

forms the Pro residue:

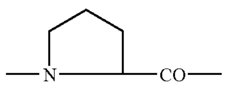

and $R_5$ represents a hydrogen atom, a pharmacologically acceptable counterion or a group capable of forming an in vivo hydrolysable phosphinic ester.

In this composition, the phosphinic pseudopeptide derivative preferably corresponds to the formula:

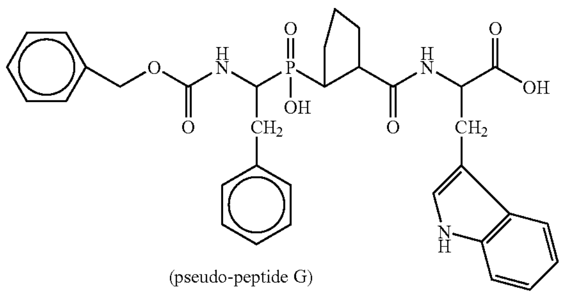

(pseudo-peptide G)

With regard to the text hereinabove, such a pharmaceutical composition is especially liable to find numerous applications in the prevention and treatment of various cardiovascular pathologies in man.

The phosphinic pseudopeptide derivatives corresponding to formula (II) mentioned above, in which $R_4$ and $R_5$ represent a hydrogen atom, may be prepared via a process comprising the following steps:

1) reacting a compound of formula (III):

(III)

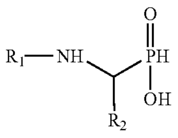

in which $R_1$ and $R_2$ are as defined above, with the compound of formula (IV):

(IV)

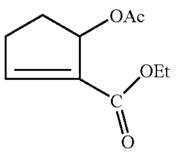

in which Ac represents the acetyl group and Et represents the ethyl group, to obtain the compound of formula (V):

(V)

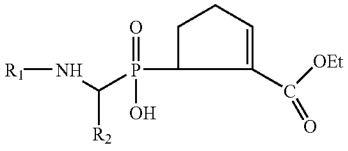

2) converting compound (V) into compound (VI) by reacting compound (V) with sodium borohydride:

(VI)

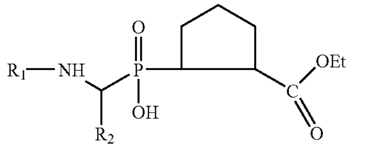

3) protecting the hydroxyl group of compound (VI) with an adamantyl group Ad to give the compound of formula (VII):

(VII)

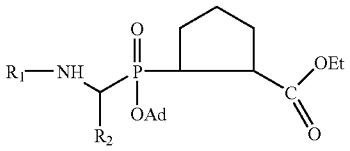

4) saponifying compound (VII) to give the compound of formula (VIII):

(VIII)

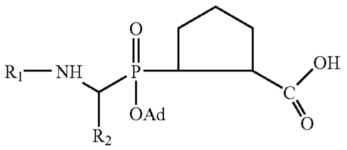

5) coupling the compound of formula (VIII) with the amino acid of formula (IX) or (X):

(IX)

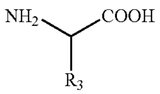

or (X)

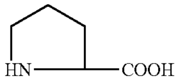

in which $R_3$ is as defined above, and 6) removing the protecting group Ad.

According to this process, the phosphinic block of formula (VIII) comprising the pseudoproline is first synthesized, and peptide coupling of this phosphinic block with the desired amino acid is then performed.

Advantageously, the peptide coupling step 5) is performed by solid-phase peptide synthesis using as solid phase a resin substituted with the amino acid of formula (IX) or (X), the N-terminal end of which will have been protected beforehand with an Fmoc (fluorenylmethoxycarbonyl) group.

If necessary, the phosphinic function of the pseudopeptide of formula (II) in which $R_5$ represents a hydrogen atom may then be esterified or salified, by reacting it with suitable reagents.

The esterification may be obtained by coupling with an alcohol of formula $R_5OH$ in which $R_5$ represents a group capable of forming an in vivo hydrolysable phosphinic ester, for example using the process described in reference [20] (method A).

The esterification may also be performed by reaction with a halide of formula $R_5X$ in which $R_5$ represents a group capable of forming an in vivo hydrolysable phosphinic ester. This reaction may be performed under alkaline conditions using the process described in reference [20] (method B).

Before performing this esterification, the carboxylic acid function(s) of the pseudopeptide is (are) protected with suitable protecting groups, which are subsequently removed using standard techniques.

When it is desired to salify the phosphinic function of the pseudopeptide of formula (II) in which $R_5$ is a hydrogen atom, to replace this hydrogen atom with a pharmaceutically acceptable counterion, the pseudopeptide is reacted with a suitable base containing this counterion, for example NaOH, KOH or $NH_4OH$.

The same technique may be used to salify the terminal carboxylic group of the pseudopeptide, in order to replace the hydrogen atom with a pharmaceutically acceptable counterion.

Other characteristics of the invention will emerge more clearly on reading the rest of the description that follows, which relates to examples for preparing pseudopeptide derivatives in accordance with the invention and for demonstrating their properties, with reference to the attached drawings.

Needless to say, this description hereinbelow is given for illustrative purposes and with no limitation of the subject of the invention.

BRIEF DESCRIPTION OF THE DRAWINGS

FIG. 3 shows the in vivo effects of pseudopeptide G on the cleavage of angiotensin I to angiotensin II.

FIG. 4 shows the in vivo effects of pseudopeptide G on the cleavage of bradykinin.

FIG. 5 shows the in vivo effects of pseudopeptide G and of RPX407 (selective inhibitor of the N-terminal site of ACE) on the cleavage of the peptide Ac-SDKP.

DETAILED DESCRIPTION OF THE EMBODIMENTS

Figure 1:
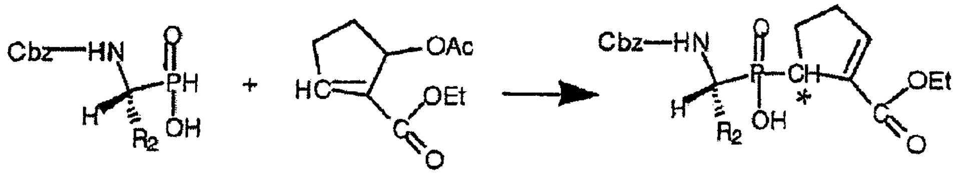
FIG. 1 shows the synthesis of synthons that are useful for the preparation of the phosphinic pseudopeptides in accordance with the invention.
Figure 1:
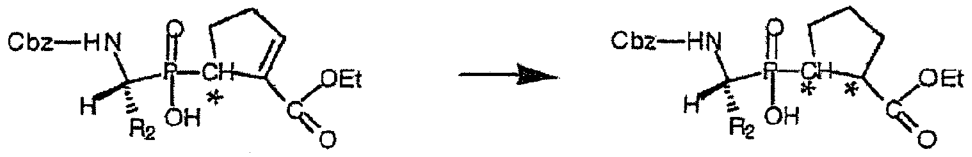
Figure 1:
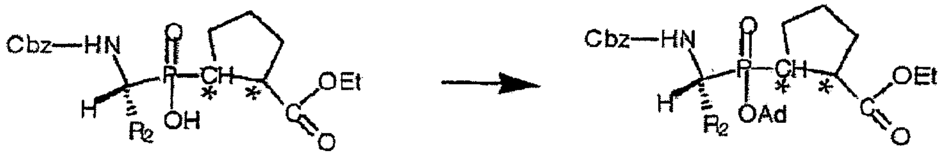
Figure 1:
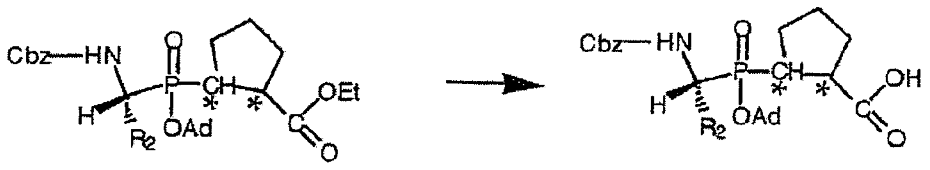

The synthesis of the phosphinic pseudopeptides was performed according to the synthetic scheme described in FIG. 1.

This figure shows the steps of the process resulting in the synthons of the formula (VIII):

(VIII)

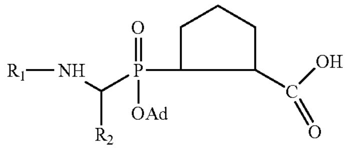

in which:

$R_1$ represents the benzyloxycarbonyl (Cbz) group, and $R_2$ is the phenyl group (compounds 1a, 3a, 4a, 5a and 6a), the phenylethyl group (compounds 1b, 3b, 4b, 5b and 6b) or the methyl group (compounds 1c, 3c, 4c, 5c and 6c).

EXAMPLE 1

Preparation of Compound 6a

1) Preparation of Compound 1a

This aminophosphinic acid derivative is prepared according to the procedure described by Baylis [18], and the enantiomer of R configuration is then obtained via recrystallization according to the protocol reported by Baylis [18].

2) Preparation of Compound 2a

This compound is obtained according to the procedure published by Villieras et al. [19]. The product obtained was characterized by NMR:

$^1$H-NMR (250 MHz, $CDCl_3$): 7.03 (t, 1H), 5.93 (m, 1H), 4.1 (m, 2H), 2.6 (m, 1H), 2.34 (m, 2H), 1.95 (s, 3H), 1.82 (m, 1H), 1.18 (t, 3H).

3) Preparation of Compound 3a

A mixture of compound 1a (3.2 g, 10 mmol) and of hexamethyldisilazane (10.5 mL, 50 mmol) under a flow of argon is heated at 110° C. for 3 hours. Compound 2 (5.5 g, 12 mmol) is added at this temperature and this solution is stirred for 4 hours at 90° C. This solution is cooled to 70° C., 10 mL of absolute ethanol EtOH are added dropwise thereto and the mixture is stirred at 70° C. for 30 minutes. After evaporating off the solvents, the residue is dissolved in 5% $NaHCO_3$ (10 mL) and 5 mL of hexane. After 3 extractions with ethyl acetate EtOAc (3×5 mL), the crude product is obtained after evaporating off the solvent. Purification on a column of silica, using a chloroform/methanol/acetic acid mixture (7/0.3/0.3) as mobile phase, gives 4 g of pure compound 3a, in the form of a white solid (89% yield).

The NMR characterization of this product is based on COSY, TOCSY and HMQC experiments:

$^1$H-NMR (250 MHz, $CDCl_3$): 1.27 (t, $^3J_{HH}$=7.1 Hz, 3H, $CH_2CH_3$), 1.95–3.00 (m, 5H, $PCH(CH_2)_2$, PhCHH), 3.13–3.45 (m, 2H, PCH, PhCHH), 4.02–4.31 (m, 2H, $CH_2CH_3$), 4.34–4.63 (m, 1H, PCH), 4.78–5.05 (m, 2H, $OCH_2Ph$), 5.71 (d, 1H, NH, $^3J_{HH}$=11.3 Hz, I), 5.78 (d, 1H, NH, $^3J_{HH}$=10.8 Hz, II), 6.91–6.99 (d, 1H, C═CH), I/II), 7.02–7.34 (m, 10H, aryl).

$^{13}$C-NMR (62 MHz, $CDCl_3$): 14.2/14.2 ($CH_2$–$CH_3$), 26.2/26.5 ($PCHCH_2$), 32.7/32.8 ($PCHCH_2CH_2$), 34.5 ($CH_2Ph$), 41.8 (d, $^1J_{PC}$=87.7 Hz, PCHC, I), 43.1 (d, $^1J_{PC}$=87.3 Hz, PCHC, II), 50.5 (d, $^1J_{PC}$=99.7 Hz, PCHN, I), 50.5 (d, $^1J_{PC}$=100.5 Hz, PCHN, II), 61.1/61.2 ($CH_2CH_3$), 66.8 ($OCH_2Ph$), 126.6, 127.7, 127.8, 127.9, 127.9, 128.4, 128.4, 129.4, 132.2, 132.3, 132.9, 136.5, 136.6, 137.1, 137.3, (aryls), 148.1 (d, $^2J_{PC}$=8.7 Hz, ═CCO, I), 148.1 (d, $^2J_{PC}$=9 Hz, ═CCO, II), 156.1 (d, $^2J_{PC}$=5.5 Hz, CONH, I), 156.2 ((d, $^2J_{PC}$=5.7 Hz, CONH, II), 165.3 (d, $^2J_{PC}$=2.7 Hz, COOEt).

$^{31}$P-NMR (100 MHz, $CDCl_3$): 46.89, 48.13.

The indications I and II correspond to the different diastereoisomers.

Elemental Analysis:

Theoretical values:

C: 61.80%, H: 6.27%, N: 3.00%.

Experimental values:

C: 61.89%, H: 6.23%, N: 2.98%

4) Preparation of Compound 4a

Compound 3a (1.4 g, 3.06 mmol) and $NiCl_2.6H_2O$ (1.09 g, 9.2 mmol) are dissolved in a mixture of THF (12.4 mL)/methanol (7.7 mL). $NaBH_4$ (0.58 g, 15.4 mmol) is added portionwise to this solution over 30 minutes, at −30° C. This mixture is stirred for a further 10 minutes at −30° C. The solvents are evaporated off and the product is extracted into a mixture of EtOAc (25 mL) and 1N HCl (20 mL, pH 1).

The organic phase is collected and washed with water (10 mL) and then dried with $Na_2SO_4$. After evaporating off the solvents, the product is purified on a column of silica with a chloroform/methanol/acetic acid (7/0.3/0.3) mobile phase. 1.28 g of compound 4a are obtained (91% yield).

The analysis by negative-mode mass spectrometry (mass observed $MH^-$=458.48, expected mass=459.47) is in accordance with the chemical structure of compound 4a.

Elemental Analysis:

Theoretical values:

C: 61.78%, H: 6.63%, N: 3.00%

Experimental values:

C: 61.98%, H: 6.31%, N: 3.08%

5) Preparation of Compound 5a

The adamantylation of compound 4a is performed according to the protocol described by Yiotakis et al. [14].

1-Adamantyl bromide (538 mg, 2.5 mmol) and $Ag_2O$ (577 mg), divided into 5 equal portions, are added over 1 hour to a solution of compound 4a (1.03 g, 2.24 mmol) in chloroform. After 2 hours, 0.5 eq of AdBr and 0.5 eq of $Ag_2O$ are added and the mixture is refluxed for 10 hours. After evaporating off the solvents, the crude product is purified on a column of silica, using a chloroform/isopropanol mixture (9.8/0.2) as mobile phase. Compound 5a is obtained in pure form in a yield of 96% (1.27 g).

Analysis by mass spectrometry, positive mode: mass observed $MH^+$=594.21, expected mass=593.1.

Elemental Analysis:

Theoretical values:

C: 67.76%, H: 7.53%, N: 2.32%

Experimental values:

C: 67.49%, H: 7.58%, N: 2.24%

6) Preparation of Compound 6a

After diluting compound 5a (1.1 g, 1.85 mmol) in methanol (20 mL), 2 mL of 4N NaOH are added. After stirring for 6 hours, TLC monitoring of the reaction confirms the complete saponification of the starting material. After evaporating off the solvent, the product is taken up in a mixture of water (10 mL) followed by addition of EtOAc (15 mL) and acidification to pH 1 with 1N HCl. The residue is taken up into the organic phase and the extraction procedure is repeated twice. The combined organic phases are dried over $Na_2SO_4$ and the solvents are then evaporated off. The pure compound 6a is obtained in a yield of 94% (0.98 g).

Analysis by mass spectrometry, positive mode: mass observed $MH^+$=566.15, expected mass=565.26.

Elemental Analysis:

Theoretical values:

C: 67.95%, H: 7.13%, N: 2.48%

Experimental values:

C: 67.64%, H: 7.30%, N: 2.40%

EXAMPLE 2

Preparation of Compound 6b

The same procedure as in Example 1 is followed to prepare compound 6b, starting with compound 1b, which is prepared according to the procedure described in [18].

The analysis by mass spectrometry of compound 6b gave the following results: expected mass=579.27, mass observed $MH^+$=580.29.

EXAMPLE 3

Preparation of Compound 6c

The same procedure as in Example 1 is followed to prepare compound 6c, starting with compound 1c, which is prepared according to the procedure described in [18].

Analysis by mass spectrometry of compound 6c gave the following results: expected mass=489.23, observed mass $MH^+$=490.11.

EXAMPLE 4

Preparation of the Pseudopeptide G of Formula

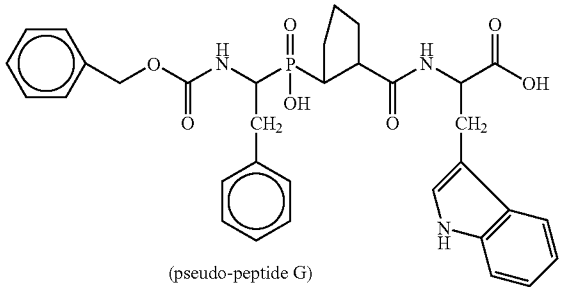

(pseudo-peptide G)

This pseudopeptide was synthesized on a solid phase using a standard protocol of solid-phase peptide synthesis. Wang resin substituted with an Fmoc-Trp (732 mg, 0.58 mmol) is suspended in N-methylpyrrolidone NMP (5 mL) and stirred for 5 minutes. After removal of the NMP by filtration, 10 mL of piperidine at a concentration of 20% in NMP are added and the mixture is stirred for 15 minutes. After filtration, the resin is washed with the following solvents: NMP (7×10 mL), $CH_2Cl_2$ (3×10 mL) and $Et_2O$ (2×10 mL). 2 ml of NMP, diisopropylethylamine DIEA (749 mg, 5.76 mmol) and compound 6a (360 mg, 0.64 mmol) diluted in NMP (2 mL) and 2-(1H)benzotriazol-1-yl)-1,1,3,3-tetramethyluronium hexafluorophosphate HBTU (730 mg, 1.92 mmol, diluted in 3 mL of NMP) are then added to the reactor. The mixture is stirred for 24 hours. After filtration, the resin is washed with NMP (4×7 mL) and $CH_2Cl_2$ (5×7 mL). A trifluoroacetic acid TFA/$CH_2Cl_2$/$H_2O$/triisopropylsilane (90/7.5/1.25/1.25) solution is then added to the reactor and the mixture is stirred for 3 hours (deprotection phase). After filtration, the filtrate containing pseudopeptide G is recovered, the solvent is evaporated off and the product is dissolved in $H_2O$. After freeze-drying, pseudopeptide G is purified by reverse-phase HPLC (Vydac column, C18, semi-preparative).

Figure 2:
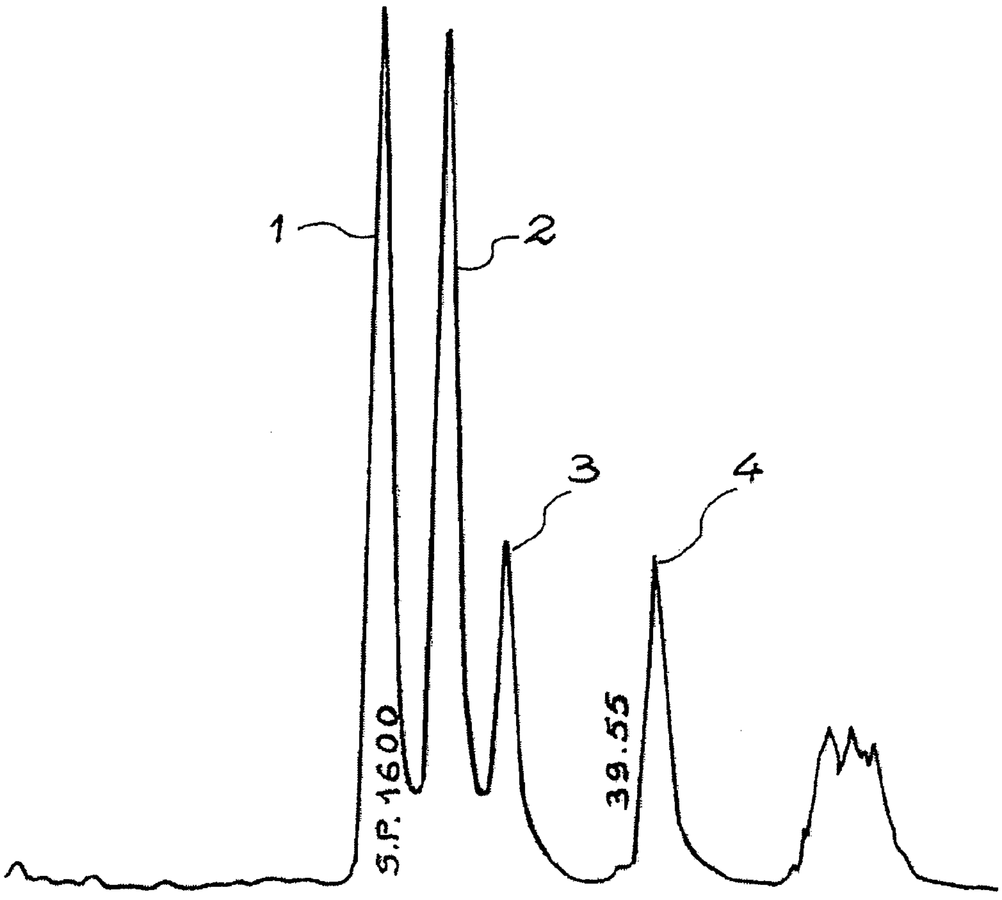
FIG. 2 shows the chromatogram obtained during the purification of the pseudopeptide G by high performance liquid chromatography (HPLC).

FIG. 2 shows the chromatogram obtained. In this figure, 4 peaks corresponding to the 4 diastereoisomers present in pseudopeptide G are observed (these 4 peaks have an identical mass spectrum, mass observed $MH^+$=618.23, expected mass=617.23). Only peak 1 shows inhibitory power with respect to ACE.

The NMR characterization of pseudopeptide G, peak 1 HPLC, is based on COSY, TOCSY and HMQC experiments:

$^1$H-NMR (250 MHz, DMSO) 4.93 (d, 2H, $CH_2$—O-Ph), 4.01 (m, 1H, CH—$CH_2$-Ph), 2.77 (m, 1H, CH—$CH_2$-Ph), 3.08 (m, 1H, CH—$CH_2$-Ph), 3.09 (α-pseudo-Proline), 1.77 (β-pseudo-Proline), 1.56 (γ-pseudo-Proline), 1.79 (δ-pseudo-Proline), 2.49 (ε-pseudo-Proline), 4.50 (α-Trp), 3.13 (β,β-Trp), 7.6 NH, 8.3 NH, aryls 7.35–6.9.

EXAMPLES 5 to 7

Preparation of Pseudopeptides B, C and D of Formulae pseudo-peptide B

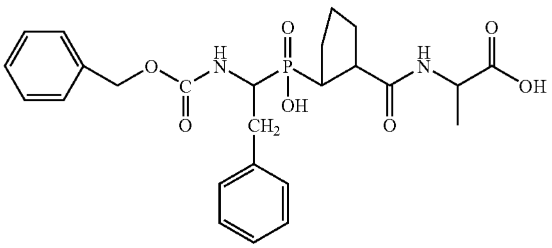

pseudo-peptide C

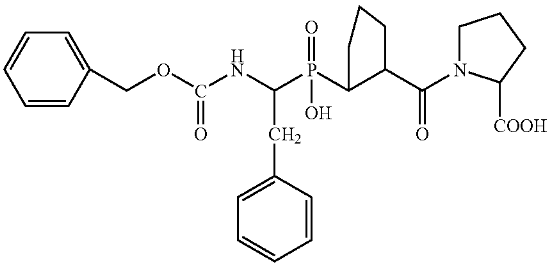

pseudo-peptide D

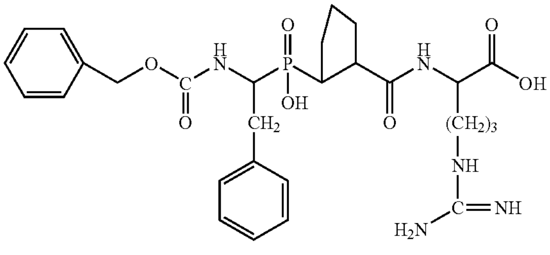

Pseudopeptides B, C and D were synthesized on a solid phase with Wang resins substituted with alanine (B), proline (C) and arginine (D), using the protocol described for the preparation of pseudopeptide G. HPLC purification of these pseudopeptides made it possible to isolate diastereoisomers of these pseudopeptides capable of inhibiting ACE.

Analysis of the pseudopeptides by mass spectrometry confirms the structure of these pseudopeptides.

Pseudopeptide B: expected mass 502.19; observed mass 503.21.

Pseudopeptide C: expected mass 528.53; observed mass 529.11.

Pseudopeptide D: expected mass 587.25; observed mass 587.24.

EXAMPLES 8 and 9

Preparation of Pseudopeptides E and F of Formulae pseudo-peptide E

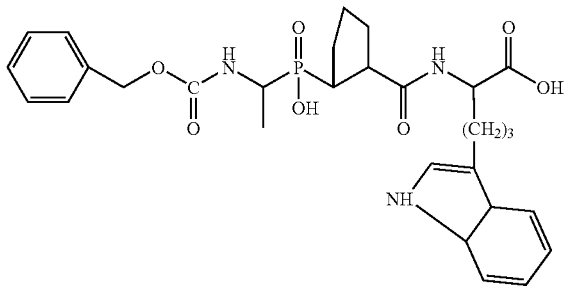

pseudo-peptide F

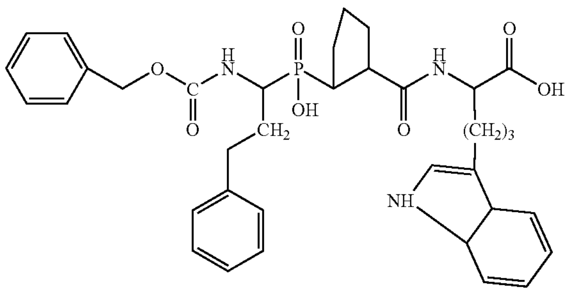

Pseudopeptides E and F are obtained via solid-phase synthesis, starting with compounds 6b and 6c and following the protocol described for the preparation of pseudopeptide G. After purification by reverse-phase C18 HPLC, the first fraction collected for each of these pseudopeptides was found to be capable of inhibiting ACE.

Analysis by mass spectrometry gave the following results:

Pseudopeptide E: expected mass 541.20; observed mass 542.26.

Pseudopeptide F: expected mass 631.24; observed mass 632.26.

EXAMPLE 10

Determination of the Inhibition Constants of Pseudopeptides A to G with Respect to the N-Terminal and C-Terminal Sites of ACE Human recombinant ACE is used for this determination. Curves of inhibition of ACE with pseudopeptides A to G are obtained using the quenched-fluorescence substrate Mca-Ala: Mca-Ala-Ser-Asp-Lys-DpaOH (Mca: 7-methoxy-coumarin-2-acetic acid; DpaOH: N-3-(2,4-dinitrophenyl)-L-2,3-diaminopropionyl).

The first fraction collected during the purification of each of the pseudopeptides A to G by HPLC (peak 1 of FIG. 2 for pseudopeptide G) is used for these tests.

From the inhibition profiles obtained with this substrate, for each pseudopeptide A to G, it is possible to determine the constants Ki N and Ki C by following the procedure described by Dive et al. [8].

The inhibition experiments were performed at 25° C., pH 6.8, 50 mM HEPES, 10 mM, $CaCl_2$, 200 mM NaCl.

The results obtained are given in the attached Table 1.

The same test with pseudopeptide A not comprising the pseudoproline residue was performed for comparative purposes. The results obtained are also given in Table 1. This pseudopeptide was prepared from the phosphinic block ZPhe[PO(OAd)—$CH_2$]AlaOH, described by Yiotakis et al. [14], followed by coupling of this block to a Wang resin substituted with the residue Fmoc-Ala.

Study of the inhibitory effects of pseudopeptides A to G on ACE and comparison of their affinity towards the N-terminal site (Ki N) and the C-terminal site (Ki C) of ACE (Table 1) allow the following conclusions to be drawn.

1°) Pseudopeptides A and B: As regards the affinity for the two active sites of ACE, the presence of a pseudoproline residue appears to be much less favourable than that of a pseudoalanine residue. On the other hand, the presence of a pseudoproline residue in position P1' of these phosphinic pseudopeptides gives access to selective inhibitors of the C-terminal site of ACE.

This result demonstrates the essential role of the pseudoproline residue to control the selectivity of the inhibitors with respect to the C-terminal site of ACE.

2°) Pseudopeptides B, C, D and G: The modifications of position P2' with the residues alanine, proline, arginine and tryptophan demonstrate that the nature of the side chain in this position is also an essential factor for selectivity. The presence of the proline residue (pseudopeptide C) generates a powerful but sparingly selective inhibitor of the N and C sites of ACE. On the other hand, the presence of a tryptophan residue makes it possible to obtain an extremely selective inhibitor (pseudopeptide G) of the C-terminal site of ACE.

3°) Pseudopeptides E and F: The substitution of a pseudophenylalanine residue in position P1 of the pseudopeptides with a pseudoalanine or pseudo-homo-phenylalanine residue leads to pseudopeptides that are less powerful and less selective than pseudopeptide G. This last result demonstrates a lesser importance of the position P1 of the inhibitors with respect to the selectivity.

The study of the pseudopeptides A to G makes it possible to conclude that, in the pseudopeptides of the invention, each position P1, P1' and P2' contributes towards the selectivity of the interactions. The presence in pseudopeptide G of the pseudophenylalanine, pseudoproline and tryptophan residues gives it particularly pronounced selectivity.

EXAMPLE 11

Demonstration of the in Vivo Properties of Pseudopeptide G

A study is performed in vivo in order to check the capacity of pseudopeptide G to inhibit the conversion of angiotensin I into angiotensin II, and to assess its effects on the cleavage of bradykinin, on the one hand, and of the peptide Ac-SDKP, on the other hand.

1) Study Protocol

This study is performed on batches of male C57BL6/J mice (Iffa Credo) weighing 20 to 23 g each, each batch comprising 6 mice.

To do this, the mice are anaesthetized by means of an intraperitoneal administration of sodium pentobarbital (Sanofi) at a dose of 80 mg/kg of body weight. The right carotid artery is isolated and a catheter (PE10, 0.28×0.61, A-M Systems, Inc.) is inserted into this artery to allow the withdrawal of blood samples, while another catheter (FEP, 0.12×0.67, Carnegie Medecin) is inserted into the ipsilateral jugular vein to allow the administration of the substances. Throughout the experiment, the body temperature of the mice is maintained at 38° C.

In a first stage, the following are administered to the mice of the same batch, via perfusion over 30 minutes:

either 50 μL of an isotonic solution (adjusted to pH 7 containing an amount of pseudopeptide G corresponding to a dose of 0.9, 3, 10 or 30 mg/kg of body weight, or 50 μL of physiological saline, or alternatively 50 μL of a solution containing an amount of perindopril corresponding to a dose of 10 mg/kg of body weight, this substance being a powerful mixed inhibitor of ACE (Servier).

Next, the following is administered as a bolus:

either a mixture comprising 2 μg of unlabelled angiotensin I and 21 μCi of $^3$H-angiotensin I in 50 μL of isotonic solution, or a mixture comprising 2 μg of unlabelled Ac-SDKP and 17 μCi of $^3$H-Ac-SDKP in 50 μL of isotonic solution, or a mixture comprising 2 μg of unlabelled bradykinin and 11 μCi of $^3$H-bradykinin in 50 μL of isotonic solution.

Samples of arterial blood, of about 50 μl, are withdrawn 30, 60 and 90 seconds after injection of the angiotensin I mixture or of the bradykinin mixture to the mice that received these mixtures, and 1, 5, 10 and 15 minutes after the start of injection of the Ac-SDKP mixture to the mice that received the latter mixture. In all cases, the blood is collected in preweighed polypropylene tubes containing 40 μL of water, 10 μL of 80% TFA and 1 μL of heparin. The exact amounts of blood withdrawn are determined by reweighing the tubes. After addition of 195 μL of distilled water, these tubes are placed in an ice bath for 10 minutes and the samples are centrifuged at 4° C. to obtain plasma extracts.

The analysis of these extracts is performed by liquid chromatography using an HPLC system (Perkin Elmer 200) linked to a radioelement detector (Z 500-4 cell, Berthold). The chromatographic separations are performed on a Kromasil C18 column (AIT), by injection of 50 μL of samples and using the following mobile phases and elution gradients:

Angiotensin I Analysis:

Mobile Phase:

solvent A: $CH_3CN/H_2O/TFA$ (10/90/0.1)

solvent B: $CH_3CN/H_2O/TFA$ (90/10/0.1)

Elution Gradients:

0–30 min: 0–30% B

30–35 min: 30–100% B

Bradykinin Analysis:

Mobile Phase:

solvent A: $CH_3CN/H_2O/TFA$ (10/90/0.1)

solvent B: $CH_3CN/H_2O/TFA$ (90/10/0.1)

Elution Gradients:

0–30 min: 0–25% B

30–35 min: 25–100% B

Ac-SDKP Analysis:

Mobile Phase:

solvent A: $H_2O/TFA$ (100/0.1)

solvent B: $CH_3CN/H_2O/TFA$ (90/10/0.1)

Elution Gradients:

0–30 min: 0–30% B

30–35 min: 30–100% B

The peaks eluted are identified by comparison of their retention times with those shown by the unlabelled substrates (angiotensin I, bradykinin and Ac-SDKP) and by the expected cleavage products (angiotensin II, BK (1-7) and BK (1-5)).

The assays are performed by integration of the area under the corresponding peaks of the chromatogram. The values thus obtained are normalized as a function of the weight of blood taken from each mouse.

The statistical comparisons of the results are performed via the non-parametric Mann-Whitney U test (Statview 5 software).

2) Results

FIG. 3 shows, in the form of a bar chart, the mean±SD values of the angiotensin II/angiotensin I ratio obtained in the case of the mice that received 0.9, 3, 10 and 30 mg of pseudopeptide G per kg of body weight (bars 0.9, 3, 10 and 30, respectively) and also the mean±SD value obtained for this same ratio in the control mice (bar T), i.e. the mice that received 50 μl of physiological saline. In this figure, * corresponds to $p<0.05$, while ** corresponds to $p<0.01$, by comparison to the control mice.

FIG. 3 demonstrates the fact that pseudopeptide G is capable of inhibiting in vivo the cleavage of angiotensin I to angiotensin II and that this inhibition is dose-dependent. Thus, the angiotensin II/angiotensin I ratio measured in the control mice is reduced by 50% in the case of the mice treated with 0.9 mg of pseudopeptide G per kg of body weight, and by 90% in the case of the mice treated with 30 mg of pseudopeptide G per kg of body weight.

FIG. 4 illustrates, in the form of a bar chart, the mean±SD percentages of protection of bradykinin obtained in the case of the mice that received 10 mg of pseudopeptide G per kg of body weight (bar G) and in the case of the control mice (bar T), i.e., in this case, the mice that received 10 mg of perindopril per kg of body weight. In this figure, ** corresponds to $p<0.01$ by comparison to the control mice.

As may be seen in FIG. 4, with the average degree of protection of bradykinin with perindopril arbitrarily set at 100%, this degree of protection is only 9.2% in the case of the mice which received 10 mg of pseudopeptide G per kg of body weight. This pseudopeptide thus appears to afford only a very moderate prevention of cleavage of bradykinin in vivo.

FIG. 5 shows, also in the form of a bar chart, the mean±SD blood concentrations (expressed in pmol/g of blood) of labelled exogenous Ac-SDKP peptide obtained in the case of the mice that received 10 mg of pseudopeptide G per kg of body weight (bar G) and in the case of the control mice (bar T), i.e. the mice that received 50 μl of physiological saline. In this figure, ** corresponds to $p<0.01$ by comparison to the control mice.

FIG. 5 also shows, for comparative purposes, the mean±SD blood concentration of labelled exogenous Ac-SDKP peptide in the case of the mice treated with 10 mg of the pseudopeptide RXP407 (described as being a selective inhibitor of the N-terminal site of ACE in references [7] and [8]) per kg of body weight (bar R) and following an identical operating protocol.

As shown by FIG. 5, pseudopeptide G, at a dose of 10 mg/kg of body weight, appears to have no significant effect on the cleavage of the peptide Ac-SDKP, whereas RXP407 increases the plasmatic content of this peptide 16-fold relative to that observed in the case of the control mice.

Thus, in vivo, pseudopeptide G very efficiently inhibits the conversion of angiotensin I to angiotensin II, without veritably preventing the degradation of bradykinin, andeven less so that of the peptide Ac-SDKP.

TABLE 1
| Formulae | Pseudo-peptide | Ki N nM ($10^{-9}$M) | Ki C nM ($10^{-9}$M) |
|---|---|---|---|
| 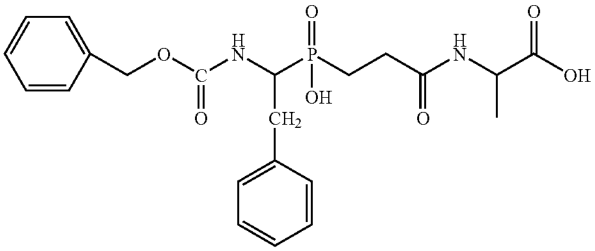 | A | 0.8 | 0.8 |
| 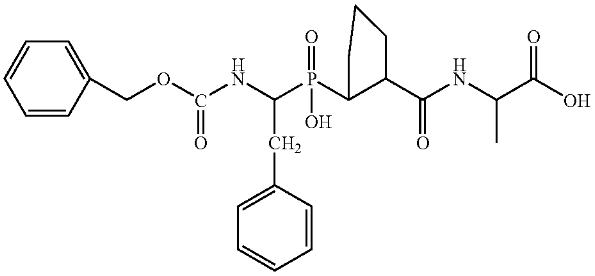 | B | 450 | 20 |
| 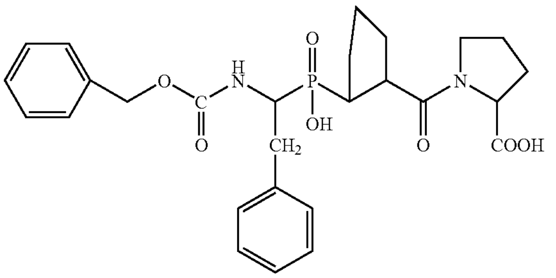 | C | 60 | 4 |
| 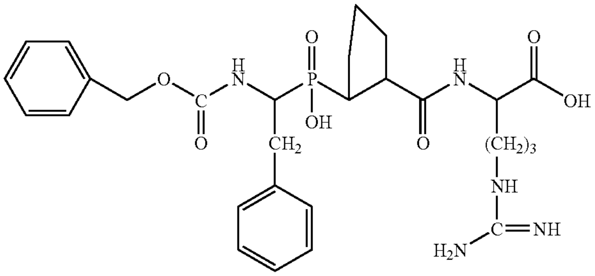 | D | 200 | 9 |
| 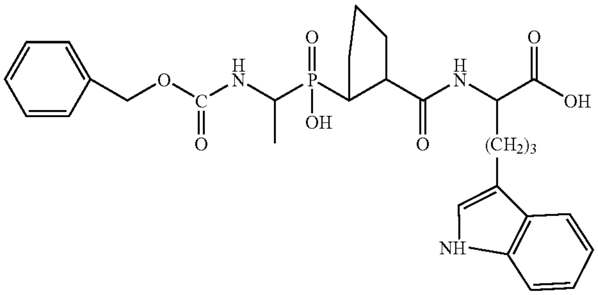 | E | 8000 | 60 |

TABLE 1-continued

| Formulae | Pseudo-peptide | Ki N nM ($10^{-9}$M) | Ki C nM ($10^{-9}$M) |
|---|---|---|---|
| 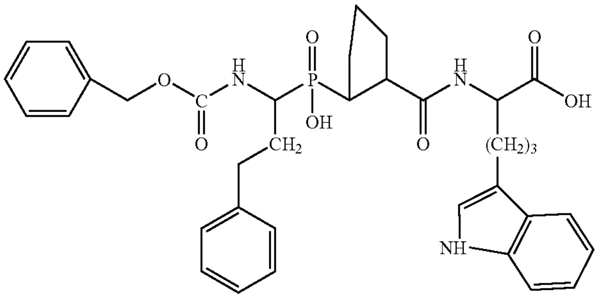 | F | 8000 | 60 |
| 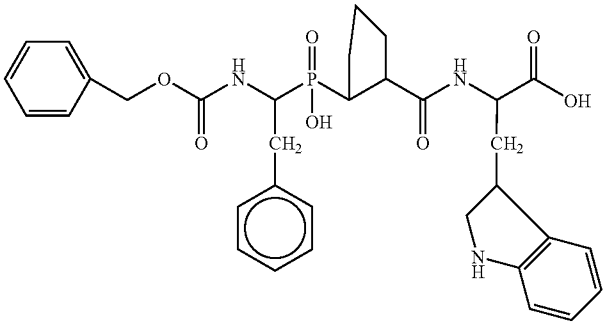 | G | 10000 | 3 |

REFERENCES

[1] Dzan V. J., 2001, *Hypertension* 37, 1047–1052.

[2] Linz W., Wiemer G., Gohlke P., Unger T., and Scholkens B. A., 1995, *Pharmacol. Rev.* 47(1), 25–49.

[3] Soubrier F., Alhenc-Gelas F., Hubert C., Allegrini J., John M., Tregear G., and Corvol P., 1988, *Proc. Natl. Acad. Sci. USA* 85(24), 9386–90.

[4] Wei L., Alhenc-Gelas F., Corvol P., and Clauser E., 1991, *J. Biol. Chem.* 266(14), 9002–8.

[5] Jaspard E., Wei L., and Alhenc-Gelas F. (1993) *J. Biol. Chem.* 268(13), 9496–503.

[6] Azizi M., Rousseau A., Ezan E., Guyene T. T., Michelet S., Grognet J. M., Lenfant M., Corvol P., and Menard J., 1996, *J. Clin. Invest.* 97(3), 839–44.

[7] WO-A-00/01706.

[8] Dive V., Cotton J., Yiotakis A., Michaud A., Vassiliou S., Jiracek J., Vazeux G., Chauvet M. T., Cuniasse P., and Corvol P. (1991) *Proc. Natl. Acad. Sci. USA* 96(8), 4330–5.

[9] Junot C., Gonzales M. F., Ezan E., Cotton J., Vazeux G., Michaud A., Azizi M., Vassiliou S., Yiotakis A., Corvol P., and Dive V., 2001, *J. Pharmacol. Exp. Ther.* 297(2), 606–11.

[10] FR-A-2 676 059.

[11] EP-A-0 725 075.

[12] Jiracek J., Yiotakis A., Vincent B., Lecoq A., Nicolaou A., Checler F., and Dive V., Development of highly potent and selective phosphinic peptide inhibitors of zinc endopeptidase 24-15 using combinatorial chemistry., 1995, *J. Biol. Chem.* 270(37): 21701–6.

[13] Jiracek J., Yiotakis A., Vincent B., Checler F. and Dive V., Development of the first potent and selective inhibitor of the zinc endopeptidase neurolysin using a systematic approach based on combinatorial chemistry of phosphinic peptides, 1996, *J. Biol. Chem.* 271(32): 19606–11.

[14] Yiotakis A., Vassiliou S., Jiracek J., and Dive V., Protection of the hydroxy-phosphinyl function of phosphinic dipeptides by adamantyl. Application to the solid-phase synthesis of phosphinic peptides, 1996, *J. Org. Chem.* 61: 6601–6605.

[15] Vassiliou S., Mucha A., Cuniasse P., Georgiadis D., Lucet-Levannier K., Beau F., Kannan R., Murphy G., Knauper V., Rio MC., Basset P., Yiotakis A., and Dive V., Phosphinic pseudo-tripeptides as potent inhibitors of matrix metalloproteinases: a structure-activity study, 1999, *J. Med. Chem.* 42(14): 2610–20.

[16] Georgiadis D., Vazeux G., Llorens-Cortes C., Yiotakis A., and Dive V., Potent and selective inhibition of zinc aminopeptidase A (EC 3.4.11.7, APA) by glutamyl aminophosphinic peptides: importance of glutamyl aminophosphinic residue in the P1 position, 2000, *Biochemistry* 39(5): 1152–5.

[17] Protective groups in Organic Synthesis, Second Edition, T. W. Green and P. G. M. Wuts, John Wiley & Sons, Inc., 309–315.

[18] Baylis E. K., Campbell C. D., and Dingwall J. G., 1984, *J. Chem. Soc. Perkin. Trans. I,* 2845.

[19] Villieras J., Rambaud W. H., and Graff M., 1986, *Synth. Commun.* 16, 149.

[20] Chen H., Noble F., Roques P., and Fournie-Zaluski M. C., 2001, *J. Med. Chem.* 44, 3523–3530.

The invention claimed is:

1. A method for selectively inhibiting the C-terminal site of angiotensin I converting enzyme comprising administering to a patient in need thereof at least one phosphinic pseudopeptide derivative comprising the amino acid sequence of formula (I):

(I)

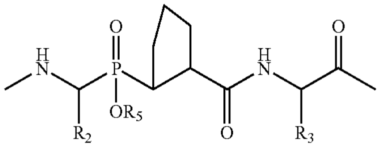

wherein, $R_2$ and $R_3$, which are identical or different, represent the side chain of a natural or unnatural amino acid, the sequence:

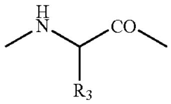

also possibly forming the Pro (proline) residue, and $R_5$ represents a hydrogen atom, a pharmacologically acceptable counterion, or a group that forms an in vivo hydrolysable phosphinic ester.

2. A method for selectively inhibiting the C-terminal site of angiotensin I converting enzyme comprising administering to a pantient in need thereof a phosphinic pseudopeptide derivative corresponding to formula (II):

(II)

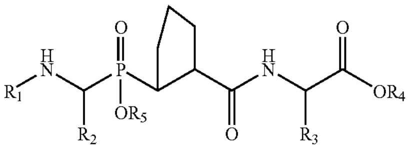

wherein, $R_1$ represents a protecting group for an amine function, or an amino acid or a peptide protected with a protecting group for an amine function, $R_2$ and $R_3$, which may be identical or different, represent the side chain of a natural or unnatural amino acid, the sequence:

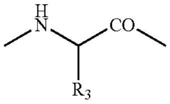

also possibly forming the Pro residue, $R_4$ represents a hydrogen atom or a pharmacologically acceptable counterion, and $R_5$ represents a hydrogen atom, a pharmacologically acceptable counterion, or a group that forms an in vivo hydrolysable phosphinic ester.

3. The method of claim 2, wherein $R_1$ represents a protecting group for an amine function chosen from acetyl and benzyloxycarbonyl groups.

4. The method of claim 1, wherein $R_2$ represents the benzyl, methyl or phenylethyl group.

5. The method of claim 1, wherein $R_3$ represents the side chain of alanine, arginine or tryptophan.

6. The method of claim 1, wherein the sequence —NH—CH($R_3$)—CO— forms the Pro residue:

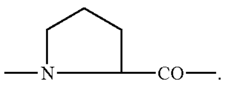

7. The method of claim 1, wherein $R_5$ represent(s) a hydrogen atom.

8. The method of claim 2, wherein the phosphinic pseudopeptide derivative is:

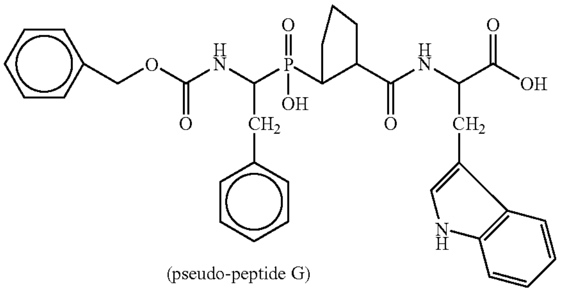

(pseudo-peptide G)

9. A phosphinic pseudopeptide derivative comprising the amino acid sequence of formula (I):

(I)

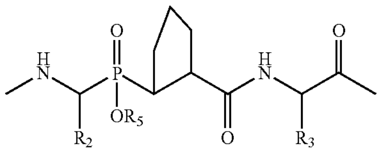

wherein, $R_2$ represents the side chain of a natural or unnatural amino acid, the sequence:

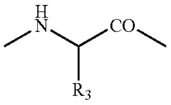

forms the Pro residue:

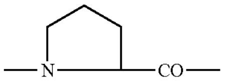

and $R_5$ represents a hydrogen atom, a pharmacologically acceptable counterion, or a group that forms an in vivo hydrolysable phosphinic ester.

10. A phosphinic pseudopeptide derivative of formula (II):

(II)

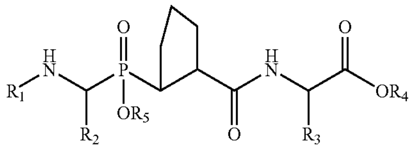

wherein, $R_1$ represents a protecting group for an amine function, or an amino acid or a peptide protected with a protecting group for an amine function, $R_2$ represents the side chain of a natural or unnatural amino acid, the sequence:

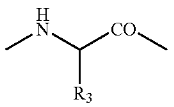

forms the Pro residue:

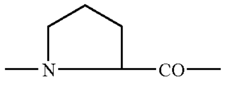

$R_4$ represents a hydrogen atom or a pharmacologially acceptable counterion, and $R_5$ represents a hydrogen atom, a pharmacologically acceptable counterion, or a group that forms an in vivo hydrolysable phosphinic ester.

11. A phosphinic pseudopeptide derivative of formula:

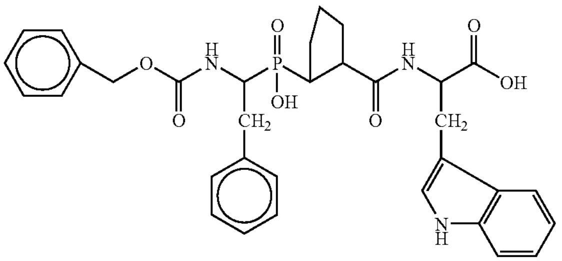

12. A pharmaceutical composition comprising at least one phosphinic pseudopeptide derivative as claimed in claim 9.

13. A pharmaceutical composition comprising a phosphinic pseudopeptide derivative of formula:

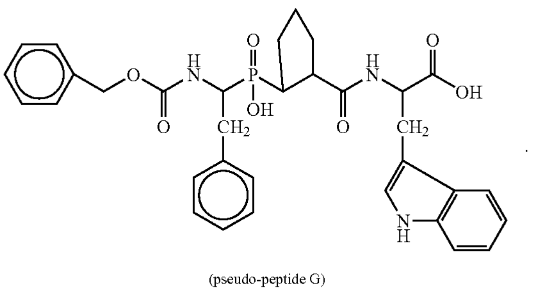

(pseudo-peptide G)

14. A process for preparing a pseudopeptide of formula:

(II)

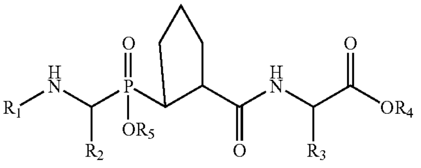

wherein:

$R_1$ represents a protecting group for an amine function, or an amino acid or a peptide protected with a protecting group for an amine function, $R_2$ and $R_3$, which may be identical or different, represent the side chain of a natural or unnatural amino acid, the sequence:

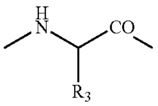

also possibly forming the Pro residue, and $R_4$ and $R_5$ represent a hydrogen atom;

which comprises the following steps:

1) reacting a compound of formula (III):

(III)

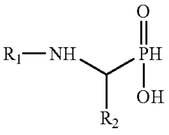

in which $R_1$ and $R_2$ are as defined above, with the compound of formula (IV):

(IV)

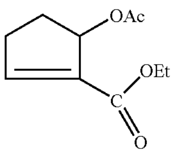

in which Ac represents the acetyl group and Et represents the ethyl group, to obtain the compound of formula (V):

(V)

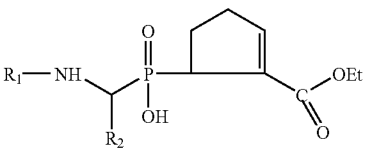

2) converting compound (V) into compound (VI) by reacting compound (V) with sodium borohydride:

(VI)

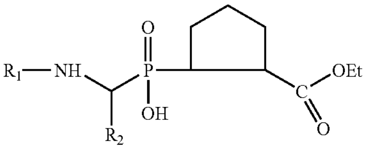

3) protecting the hydroxyl group of compound (VI) with a protecting group $R_5$ to give the compound of formula (VII):

(VII)

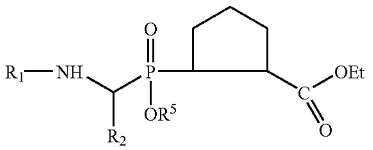

4) saponifying compound (VII) to give the compound of formula (VIII):

(VIII)

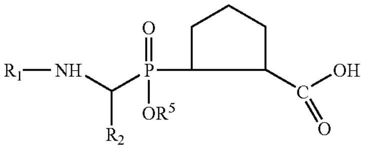

5) coupling the compound of formula (VIII) with the amino acid of formula (IX) or (X):

(IX)

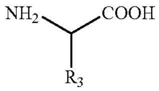

or (X)

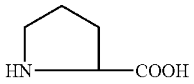

in which $R_3$ is as defined above, and 6) removing the protecting group $R^5$.

15. A process as claimed in claim 14, wherein the peptide coupling step 5) is performed via solid-phase peptide synthesis wherein the solid phase is a resin substituted with the amino acid of formula (IX) or (X).

16. A process for preparing a pseudopeptide of formula:

(II)

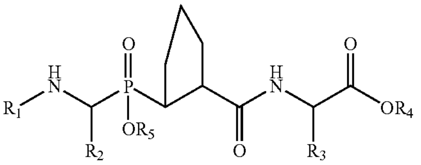

wherein, $R_1$ represents a protecting group for an amine function, or an amino acid or a peptide protected with a protecting group for an amine function, $R_2$ and $R_3$, which may be identical or different, represent the side chain of a natural or unnatural amino acid, the sequence:

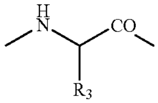

also possibly forming the Pro residue, $R_4$ represents a hydrogen atom, and $R_5$ represents a group that forms an in vivo hydrolysable phosphinic ester;

wherein the phosphinic function of the pseudopeptide obtained via the process of claim 14 is esterified by coupling with an alcohol of formula $R_5OH$ or by reaction with a halide of formula $R_5X$ in which X represents a halogen atom.

17. A compound of formula (VIII):

(VIII)

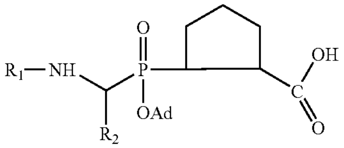

wherein:

Ad represents an adamantyl group, $R_1$ represents a protecting group for an amine function or an amino acid or a peptide protected with an amine function, and $R_2$ represents the side chain of a natural or unnatural amino acid.

18. The method of claim 2, wherein $R_2$ represents the benzyl, methyl or phenylethyl group.

19. The method of claim 2, wherein $R_3$ represents the side chain of alanine, arginine or tryptophan.

20. The method of claim 2, wherein the sequence —NH—CH($R_3$)—CO— forms the Pro residue:

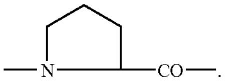

21. The method of claim 2, wherein $R_4$ and/or $R_5$ represent(s) a hydrogen atom.

22. A pharmaceutical composition comprising at least one phosphinic pseudopeptide derivative as claimed in claim 10.

23. A pharmaceutical composition comprising at least one phosphinic pseudopeptide derivative as claimed in claim 11.

24. A process for preparing a pseudopeptide of formula:

(II)

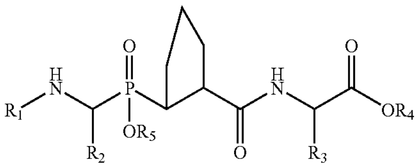

wherein, $R_1$ represents a protecting group for an amine function, or an amino acid or a peptide protected with a protecting group for an amine function, $R_2$ and $R_3$, which may be identical or different, represent the side chain of a natural or unnatural amino acid, the sequence:

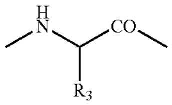

also possibly forming the Pro residue, $R_4$ represents a hydrogen atom, and $R_5$ represents a group that forms an in vivo hydrolysable phosphinic ester;

wherein the phosphinic function of the pseudopeptide obtained via the process of claim 15 is esterified by coupling with an alcohol of formula $R_5OH$ or by reaction with a halide of formula $R_5X$ in which X represents a halogen atom.

25. A process as claimed in claim 14, wherein $R^5$ is an adamantyl group.

* * * * *

SEQUENCE LISTING

<160> NUMBER OF SEQ ID NOS: 5

<210> SEQ ID NO 1
<211> LENGTH: 10
<212> TYPE: PRT
<213> ORGANISM: Homo Sapiens

<400> SEQUENCE: 1

Asp Arg Val Tyr Ile His Pro Phe His Leu
1 5 10

<210> SEQ ID NO 2
<211> LENGTH: 8
<212> TYPE: PRT
<213> ORGANISM: Homo Sapiens

<400> SEQUENCE: 2

Asp Arg Val Tyr Ile His Pro Phe
1 5

<210> SEQ ID NO 3
<211> LENGTH: 9
<212> TYPE: PRT
<213> ORGANISM: Homo Sapiens

<400> SEQUENCE: 3

Arg Pro Pro Gly Phe Ser Pro Phe Arg
1 5

<210> SEQ ID NO 4
<211> LENGTH: 7
<212> TYPE: PRT
<213> ORGANISM: Homo Sapiens

<400> SEQUENCE: 4

Arg Pro Pro Gly Phe Ser Pro
1 5

<210> SEQ ID NO 5
<211> LENGTH: 4
<212> TYPE: PRT
<213> ORGANISM: Homo Sapiens

<400> SEQUENCE: 5

Ser Asp Lys Pro
1